United States Patent
Lee et al.

(10) Patent No.: US 10,494,411 B2
(45) Date of Patent: Dec. 3, 2019

(54) FUSION PROTEIN COMPRISING TRANSCRIPTION MODULATION DOMAIN OF P65 AND PROTEIN TRANSDUCTION DOMAIN, AND USES THEREOF

(71) Applicant: GOOD T CELLS, INC., Seoul (KR)

(72) Inventors: Sang-Kyou Lee, Seoul (KR); Sung-Dong Park, Seoul (KR)

(73) Assignee: Good T Cells, Inc., Seoul (KR)

( * ) Notice: Subject to any disclaimer, the term of this patent is extended or adjusted under 35 U.S.C. 154(b) by 44 days.

(21) Appl. No.: 15/342,264

(22) Filed: Nov. 3, 2016

(65) Prior Publication Data

US 2017/0101448 A1  Apr. 13, 2017

(30) Foreign Application Priority Data

Oct. 12, 2015 (KR) .................. 10-2015-0142144

(51) Int. Cl.
| | | |
|---|---|---|
| *A61K 38/00* | (2006.01) | |
| *A61P 5/00* | (2006.01) | |
| *C07K 14/47* | (2006.01) | |
| *C07K 14/705* | (2006.01) | |

(52) U.S. Cl.
CPC ........ *C07K 14/4702* (2013.01); *C07K 14/705* (2013.01); *A61K 38/00* (2013.01); *C07K 2319/10* (2013.01); *C07K 2319/70* (2013.01); *C07K 2319/80* (2013.01)

(58) Field of Classification Search
CPC ......... A61K 38/00; A61P 35/00; C07K 14/47; C07K 2319/00; C07K 14/705
See application file for complete search history.

(56) References Cited

U.S. PATENT DOCUMENTS

2013/0231274 A1*  9/2013  Lee ..................... C12N 15/62
514/1.7

OTHER PUBLICATIONS

Uretsky, Antiviral drug, Gale Encyclopedia of Children's Health: Infancy through Adolescence, 2006, Encyclopedia.com, available online at http://www.encyclopedia.com/topic/antiviral_drug.aspx, accessed May 26, 2016. (Year: 2006).*

Spero, Type 1 Diabetes in Adults: Can It Be Prevented?, available online at https://www.diabetesselfmanagement.com/blog/type-1-diabetes-adults-can-prevented/print/, accessed on Nov. 5, 2018. (Year: 2018).*

Mercola, Crohn's Disease Prevention: How to Avoid Falling Victim to This Disease, available online at https://articles.mercola.com/crohns-disease/prevention.aspx, accessed on Nov. 5, 2018. (Year: 2018).*

Protein A001645, Signaling Gateway—UCSD Molecule Pages, available online at http://www.signaling-gateway.org/molecule/query?afcsid= A001645, accessed on Nov. 5, 2018. (Year: 2018).*

Park, "Therapeutic effect of transducible Smad3 and p65 transcription modulation domain in inflammatory diseases", A Dissertation submitted to the Division of Life Science & Biotechnology and the Graduate School of Yonsei University (2015).

Park et al., "Intranuclear interactomic inhibition of NF-kB suppresses LPS-induced severe sepsis", Biochemical and Biophysical Research Communications, 464:711-717 (2015).

* cited by examiner

*Primary Examiner* — Kaipeen E Yang
(74) *Attorney, Agent, or Firm* — McDonnell Boehnen Hulbert & Berghoff LLP (57) ABSTRACT

The present invention relates to a novel fusion protein comprising the transcription modulation domain of the transcription factor NF-κB subunit p65 and a protein transduction domain and to the use thereof. The fusion protein of the present invention has the effects of inhibiting the transcription of NF-κB and IL-2 by competitive inhibition and inhibiting the LPS-induced secretion of inflammatory cytokines and also inhibiting the production of IL-2, IFN-γ, IL-4, IL-17A and IL-10 in splenocytes, and thus is effectively used as a composition for the prevention or treatment of a disease related to NF-κB overactivity.

2 Claims, 9 Drawing Sheets

Specification includes a Sequence Listing.

M: Marker
Lane1: p65-TMD
Lane2: nt-p65-TMD
Lane3: mnt-p65-TMD

… can bind to a target promoter, but cannot promote transcription. Accordingly, the fusion protein of the present invention is a dominant negative mutant for the NF-κB gene, and thus can act as a competitive inhibitor against wild-type NF-κB in cells to inhibit the transcription and activity of NF-κB.

In one embodiment, NF-κB that is used in the present invention is NF-κB selected from the group consisting of RelA (p65), c-Rel, Rel-B, NF-κB1 (p50) and NF-κB2 (p52). In a specific embodiment, NF-κB that is used in the present invention is RelA (p65).

In one embodiment, the transcription modulation domain of NF-κB that is used in the present invention comprises an amino acid sequence of SEQ ID NO: 1. In another embodiment of the present invention, the transcription modulation domain of NF-κB, which comprises the amino acid sequence of SEQ ID NO: 1, is encoded by a nucleotide sequence of SEQ ID NO: 3.

As used herein, the term "protein transduction domain" is a short, strongly hydrophobic peptide consisting of 7-50 amino acids, and means a domain capable of transducing not only a protein having a molecular weight of 120 kDa or more, but also DNA or RNA, into cells. As demonstrated in the examples below, it could be seen that, unlike the fusion protein of the present invention, a protein to which the protein transduction domain of the present invention is not attached (that is, p65-TMD composed only of the transcription modulation domain) has no effects on the inhibition of transcription of NF-κB and IL-2, the inhibition of LPS-induced secretion of inflammatory cytokines, and the inhibition of production of IL-2, IFN-γ, IL-4, IL-17A and IL-10 in splenocytes.

According to one embodiment of the present invention, the protein transduction domain that is used in the present invention is selected from the group consisting of Hph-1, Mph-1, Sim-2, Tat, VP22, Antp (antennapedia), Pep-1 (peptide-1), PTD-5 (protein transduction domain-5), 11R, 7R and CTP (cytoplamic transduction peptide). As used herein, the terms "11R" and "7R" mean peptides consisting of 11 and 7 arginine residues, respectively. According to a specific embodiment, the protein transduction domain that is used in the present invention is Hph-1.

According to one embodiment of the present invention, the protein transduction domain that is used in the present invention comprises an amino acid sequence of SEQ ID NO: 2. According to another embodiment of the present invention, the protein transduction domain comprising the amino acid sequence of SEQ ID NO: 2 according to the present invention is encoded by a nucleotide sequence of SEQ ID NO: 4.

According to one embodiment of the present invention, the fusion protein of the present invention comprises an amino acid sequence of SEQ ID NO: 5. According to a specific embodiment of the present invention, a fusion protein comprising an amino acid sequence of SEQ ID NO: 5 is encoded by a nucleotide sequence of SEQ ID NO: 6.

Figure 6:
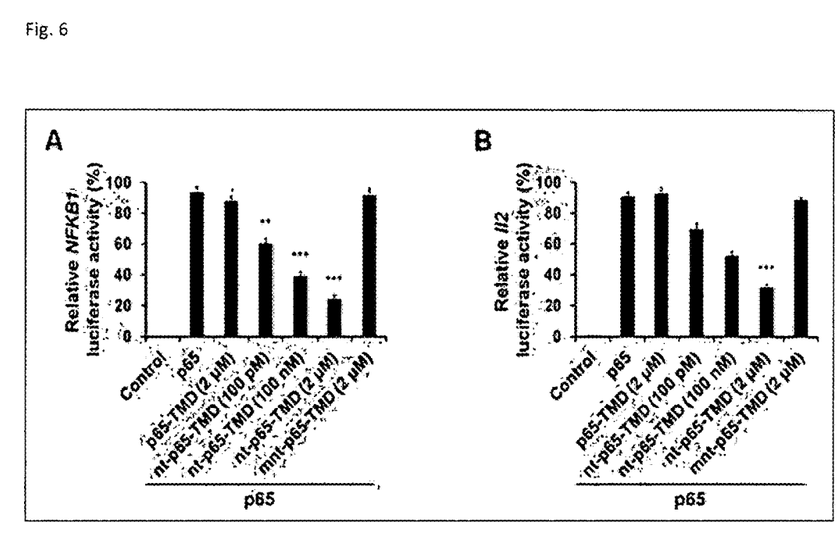
FIG. 6 shows the effect of the fusion protein (nt-p65-TMD) of the present invention on competitive inhibition of transcription.

In accordance with another aspect of the present invention, there is provided an inhibitor of NF-κB transcription or activity, comprising the fusion protein of the present invention. As demonstrated in the examples below, it was shown that the fusion protein of the present invention could inhibit the transcription and activity of NF-κB and IL-2 (FIG. 6), inhibit the LPS-induced secretion of inflammatory cytokines (FIG. 7), and inhibit the production of IL-2, IFN-γ, IL-4, IL-17A and IL-10 which are expressed by T-cell activation stimulated by anti-CD3/CD28 in splenocytes (FIG. 9), indicating that the fusion protein can inhibit the NF-κB-induced proliferation and differentiation of T cells and the NF-κB-induced secretion of inflammatory cytokines. This suggests that the fusion protein of the present invention can effectively prevent, alleviate or treat a disease caused by the overactivity of NF-κB.

In accordance with another aspect of the present invention, there is provided a pharmaceutical composition for the prevention or treatment of a disease related to NF-κB overactivity, the pharmaceutical composition comprising the fusion protein of the present invention as an active ingredient.

As demonstrated in the examples below, the fusion protein of the present invention inhibits the transcription of NF-κB and IL-2, inhibits the LPS-induced secretion of inflammatory cytokines, and inhibits the production of IL-2, IFN-γ, IL-4, IL-17A and IL-10 in splenocytes. Thus, the fusion protein of the present invention may be effectively used as a composition for efficiently preventing or treating various diseases related to NF-κB overactivity.

Figure 10:
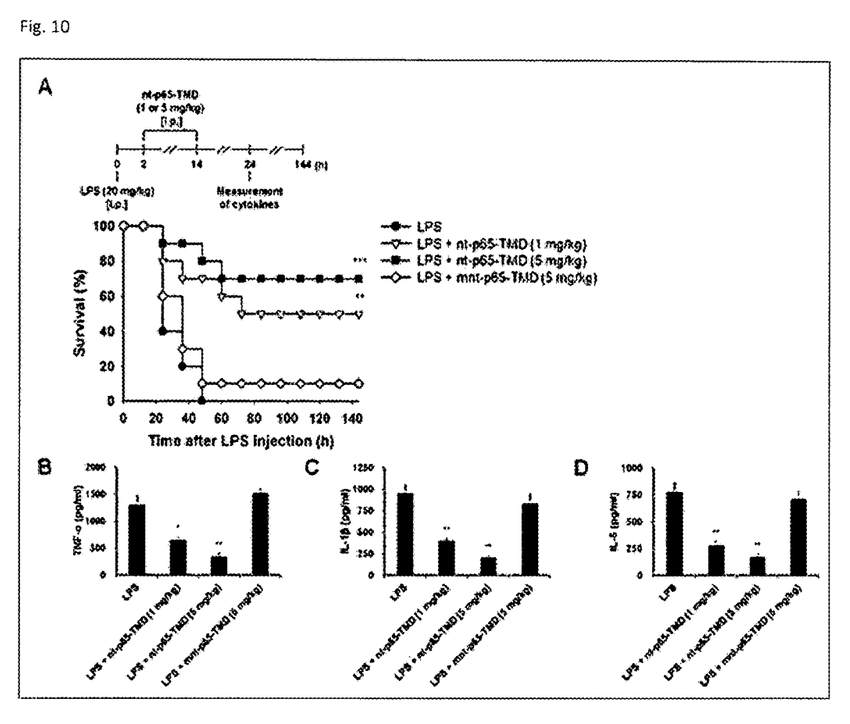
FIG. 10 shows results indicating that the fusion protein (nt-p65-TMD) of the present invention inhibits the secretion of inflammatory cytokines (TNF-α, IL-1β and IL-6) in septic shock animal models to thereby increase the survival rate of the animal models.

In one embodiment of the present invention, the disease related to NF-κB overactivity in the present invention is an inflammatory disease or an autoimmune disease. In another embodiment of the present invention, the disease related to NF-κB overactivity in the present invention is a disease selected from the group consisting of septic shock, allergic asthma, allergic nasitis, atopic dermatitis, systemic lupus erythematosus, rheumatoid arthritis, ulcerative colitis, dacryoadenitis, Alzheimer's disease, stroke, arteriosclerosis, vascular restenosis, type I diabetes, type II diabetes, urticaria, conjunctivitis, psoriasis, systemic inflammatory response syndrome, polymyositis, dermatomyositis, polyarthritis nodosa, mixed connective tissue disease, Sjogren's syndrome, gout, Parkinson's disease, amyotrophic lateral sclerosis, diabetic retinopathy, multiple sclerosis, Crohn's disease, chronic thyroiditis, Celiac disease, myasthenia gravis, pemphigus vulgaris, viral diseases, bacterial diseases, radiation-induced disorders, arteriosclerosis, hemangioma, angiofibroma, reperfusion injury, and cardiac hypertrophy. According to a specific embodiment, the disease related to NF-κB overactivity in the present invention is septic shock. Septic shock that causes a severe systemic inflammatory reaction due to microbial infection shows abnormalities in the cardiovascular system and vasomotor factors by endotoxins and inflammatory mediators circulating the blood vessels. For this reason, hypovolemia occurs due to dehydration and leakage of intravascular liquid, and vascular contraction and relaxation in capillary vessels occur to cause abnormalities in blood supply, and vasculitis and thrombosis make tissue reflux more difficult, resulting in tissue hypoxia and metabolic acidosis. In particular, endotoxins activate NF-κB in immunocytes (macrophages, granulocytes, dendritic cells, and lymphocytes) to secrete cytokines such as tumor necrosis factor, linterleukin-1 and linterleukin-6, and such cytokines stimulate neutrophils, endothelial cells, platelets or inflammatory mediator-releasing cells to cause systemic reactions. As demonstrated in the examples below, it was shown that the fusion protein of the present invention inhibited the secretion of inflammatory cytokines in septic shock models induced by LPS and increased the survival rate of the models (FIG. 10).

Thus, it can be seen that the fusion protein of the present invention is effective for the prevention or treatment of a disease related to NF-κB overactivity.

If the composition of the present invention is prepared as a pharmaceutical composition, the pharmaceutical composition of the present invention contains a pharmaceutically acceptable carrier. Examples of the pharmaceutically acceptable carrier that is contained in the pharmaceutical composition of the present invention include, but are not limited to, lactose, dextrose, sucrose, sorbitol, mannitol, starch, acacia gum, calcium phosphate, alginate, gelatin, calcium silicate, microcrystalline cellulose, polyvinyl pyrrolidone, cellulose, water, syrup, methyl cellulose, methyl hydroxybenzoate, propyl hydroxybenzoate, talc, magnesium stearate, and mineral oil, which are commonly used in formulations. The pharmaceutical composition may further contain, in addition to the above-described components, a lubricant, a wetting agent, a sweetening agent, a flavoring agent, an emulsifying agent, a suspending agent, a preservative or the like. Suitable pharmaceutically acceptable carriers and formulations are described in detail in Remington's Pharmaceutical Sciences (19$^{th}$ ed., 1995).

The pharmaceutical composition of the present invention may be administered orally or parenterally. When the pharmaceutical composition is administered parenterally, it may be injected intravenously, subcutaneously, intramuscularly, intraperitoneally, transdermally, or the like. In one embodiment of the present invention, the pharmaceutical composition of the present invention may be administered by intraperitoneal injection.

The suitable dose of the pharmaceutical composition of the present invention may vary depending on various factors, including the formulation method, the mode of administration, the patient's age, weight, sex, disease condition and diet, the time of administration, the route of administration, the rate of excretion, and reaction sensitivity. The daily dose of the pharmaceutical composition according to the present invention is, for example, 0.0001-1000 mg/kg.

The pharmaceutical composition of the present invention may be formulated with a pharmaceutically acceptable carrier and/or excipient in a unit dosage form or a multiple dosage form, according to a method that can be easily carried out by a skilled person in the art to which the present invention pertains. Herein, the formulation may be a solution in oil or an aqueous medium, a suspension, syrup, an emulsifying solution, an extract, powder, granules, a tablet, or a capsule, and may further contain a dispersing agent or a stabilizing agent.

Because the NF-κB transcription or activity inhibitor of the present invention and the composition for the prevention or treatment of a disease related to NF-κB overactivity according to the present invention commonly comprise the above-described fusion protein, the description of the contents that are common in relation to the fusion protein is omitted in order to avoid excessive complexity of description.

DESCRIPTION OF SPECIFIC EMBODIMENTS

Hereinafter, the present invention will be described in further detail with reference to examples. It will be obvious to those skilled in the art that these examples are for illustrative purposes and are not intended to limit the scope of the present invention.

EXAMPLES

Figure 1:
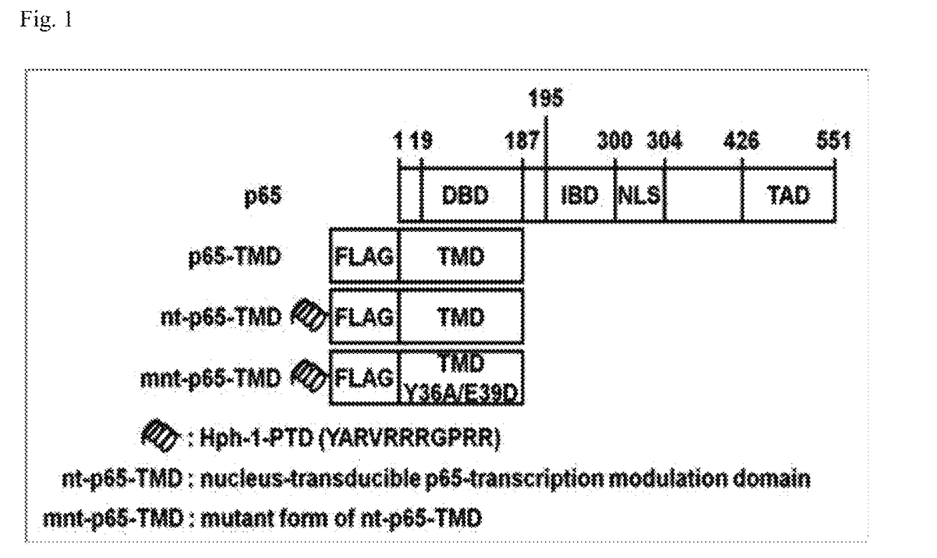
FIG. 1 shows the structure of a fusion protein (nt-p65-TMD) of a p65-transcription modulation domain (p65-TMD) and Hph-1 (PTD) according to an embodiment of the present invention. DBD: DNA binding domain; IBD: IκB binding domain; NLS: nuclear localization sequence; TAD: transactivation domain.
Figure 2:
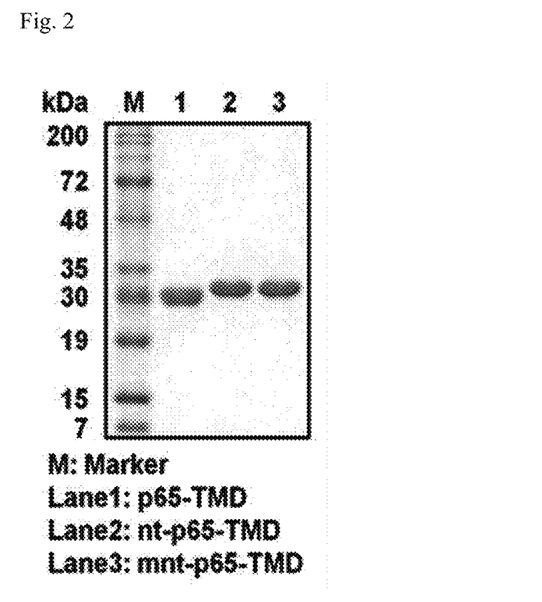
FIG. 2 shows the results of Coomassie blue staining of the fusion protein (nt-p65-TMD) according to the present invention.

Example 1: Preparation of a Recombinant Fusion Protein Comprising p65 Transcription Modulation Domain and Protein Transduction Domain The protein transduction domain (PTD) Hph-1 (SEQ ID NO: 4) was cloned into the p65 transcription modulation domain p65-TMD (SEQ ID NO: 2) and a pET-28a(+) vector (Novagen) to thereby construct a recombinant fusion DNA (nt-p65-TMD) (SEQ ID NO: 6). The recombinant fusion DNA was transformed into a BL21 CodonPlus(DE3)-RIPL E. coli strain (Invitrogen). The transformed strain was cultured, and then treated with 1 mM IPTG (isopropyl-β-D-thiogalactopyranoside, Duchefa), after which protein expression in the strain was induced at 37° C. for 5 hours. Next, only the cells were harvested, lysed with lysis buffer (10 mM imidazole, 50 mM NaH$_2$PO$_4$, 300 mM NaCl, pH 8.0), and then disrupted with a homogenizer. The fusion protein was bound to Ni-NTA beads (Qiagen) by 6 histidine residues linked to the upstream region of the protein. The protein was loaded onto HisTrap chromatography columns (Bio-Rad), and washed sufficiently with washing buffer (30 mM imidazole, 50 mM NaH$_2$PO$_4$, 300 mM NaCl, pH 8.0), and the protein was eluted with elution buffer (250 mM imidazole, 50 mM NaH$_2$PO$_4$, 300 mM NaCl and pH 8.0). Using PD-10 Sephadex G-25 (GE Healthcare), imidazole and NaCl were removed while the buffer was replaced with 10% glycerol-containing PBS. Because the obtained protein contained endotoxins such as LPS, it was purified once more using SP beads (SP Sepharose™ Fast Flow, GE Healthcare) to remove the endotoxins. The resulting protein was bound using binding buffer (50 mM NaH$_2$PO$_4$, 300 mM NaCl, pH 6.0), and then loaded onto a column and eluted with elution buffer (50 mM NaH$_2$PO$_4$, 2 M NaCl, pH 6.0). Finally, NaCl was removed using PD-10 Sephadex G-25, and the buffer was placed with 10% glycerol-containing PBS, after which the resulting protein (SEQ ID NO: 5, recombinant fusion protein) was stored at 80° C. until use in experiments (see FIGS. 1 and 2).

Example 2: Analysis of Intracellular Transduction of Nt-p65-TMD Recombinant Fusion Protein 2-1: Analysis of Intracellular Transduction by Western Blotting BV2 microglial cells and Jurkat T cells were incubated with the recombinant fusion protein (nt-p65-TMD) at varying protein concentrations (0, 0.1, 0.5, 1, 2 and 5 µM) or for varying times (0, 1, 2, 4, 6, 12, 24 and 48 hours), and whether or not the fusion protein was transduced was analyzed by Western blotting.

Figure 3A:
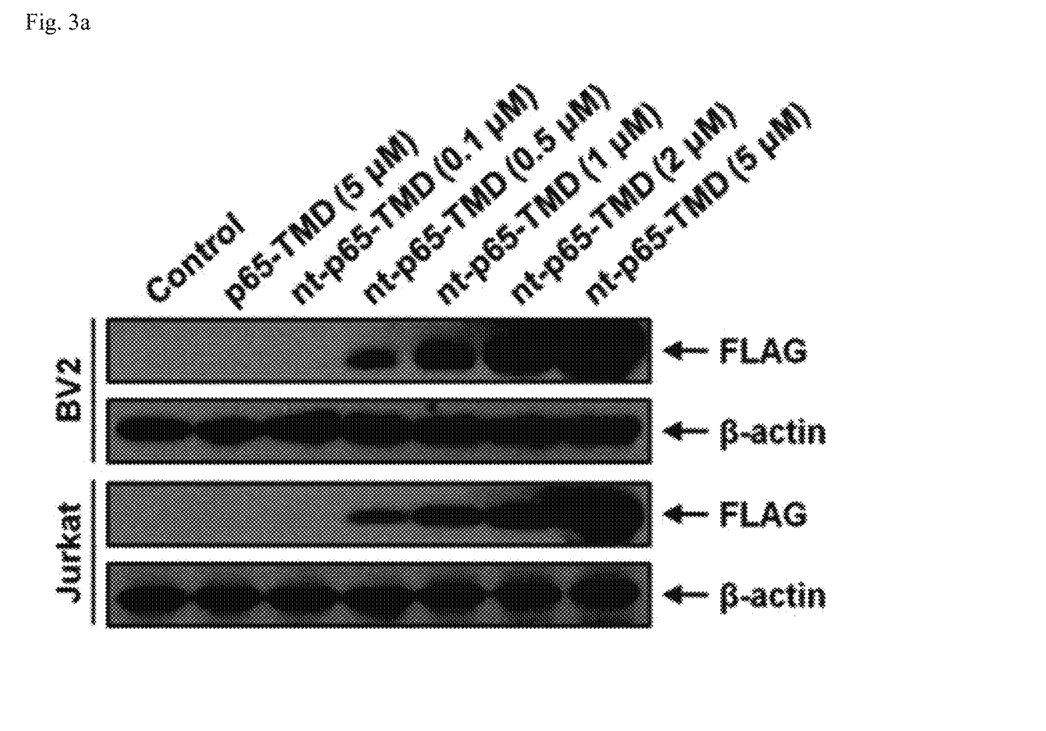
FIG. 3 shows the results of transduction of the fusion protein (nt-p65-TMD) of the present invention into BV2 and Jurkat T cells.
Figure 3B:
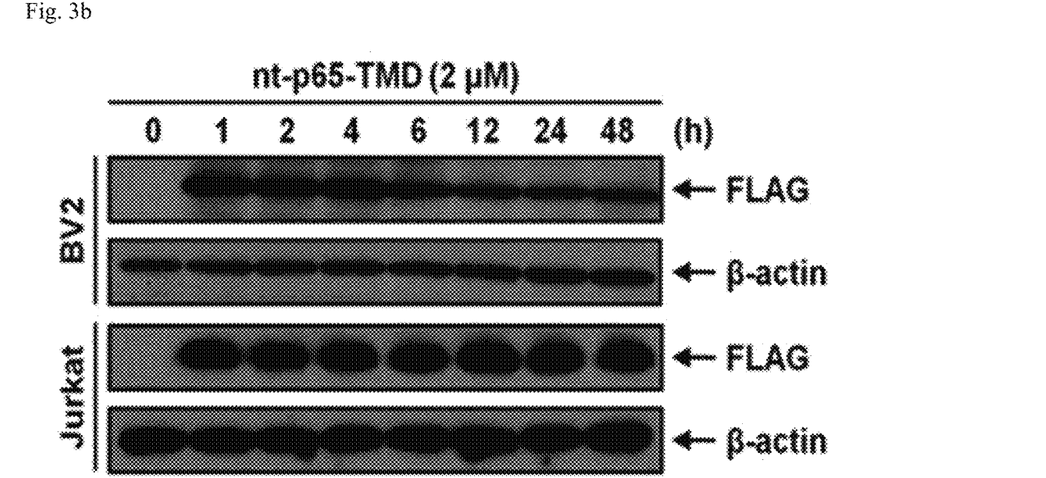

As a result, it was shown that the fusion protein was well transduced in proportion to the concentration thereof and was continuously transduced even at 48 hours while the protein in the cell culture maintained its structure (see FIG. 3).

2-2: Analysis of Whether or not Fusion Protein is Transduced to Nucleus of Cells, by Use of Antibody 5 µM of the recombinant fusion protein (nt-p65-TMD) of Example 1 was incubated with BV2 microglial cells and HeLa cells for 1 hour and washed with PBS, after which the cells were treated with 0.2% Triton X-100 (Sigma-Aldrich) to form an opening, and a fluorescence-labeled antibody was bound to the recombinant fusion protein through the opening. Next, the nucleus of the cells was stained with DAPI dye (Invitrogen), and then the location of fluorescence was determined by a fluorescence microscope to thereby determine the location to which the recombinant fusion protein was transduced.

Figure 4:
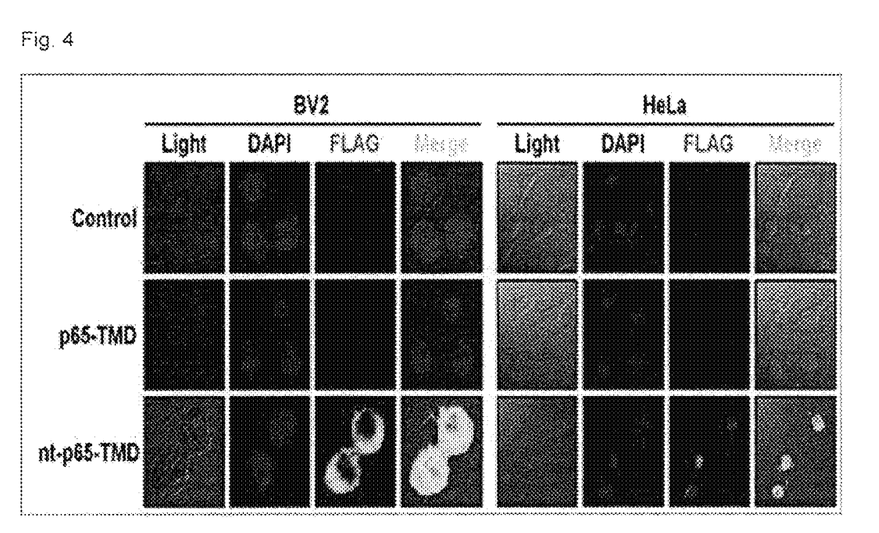
FIG. 4 shows the results of transduction of the fusion protein (nt-p65-TMD) of the present invention into the nuclei of BV2 and HeLa cells.

As a result, it was shown that the fusion protein was well transduced to the nucleus of the cells by the property of the PTD (see FIG. 4).

Example 3: Analysis of Cytotoxicity of nt-p65-TMD Recombinant Fusion Protein

In order to confirm that the protein obtained from the *E. coli* strain by expression is completely free of LPS so that it is not toxic to cells or animals, a cytotoxicity test was performed. Varying concentrations of the protein were transduced into BV2 microglial cells and splenocytes, and then the cells were incubated with WST-8, a substrate that develops color by dehydrogenase present in living cells.

Figure 5:
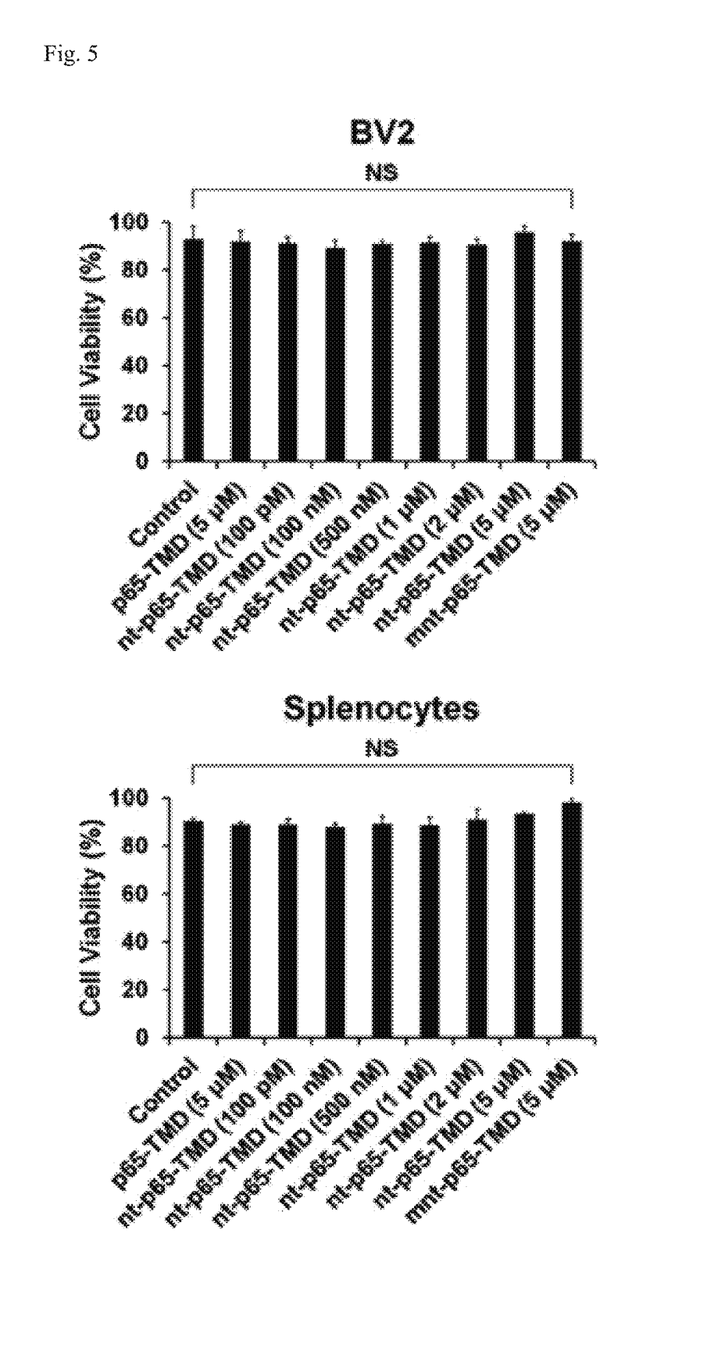
FIG. 5 shows the results of cytotoxicity of the fusion protein (nt-p65-TMD) of the present invention in BV2 and spleen cells.

As a result, it could be seen that the cells treated with the fusion protein showed no cytotoxicity regardless of the concentration of the fusion protein, unlike cells not treated with the protein (FIG. 5).

Example 4: Confirmation of the Effect of nt-p65-TMD Recombinant Fusion Protein on Specific Inhibition of Transcription Factor 4-1: Confirmation of Inhibitory Effect against Transcription of NF-κB and IL-2 in HEK293T Cells To directly confirm whether or not the nt-p65-TMD recombinant fusion protein of Example 1 binds to the promoters of the NF-κB and IL-2 cytokine genes in place of wild-type p65 to inhibit the expression of the genes, luciferase reporter gene was used. First, each of NF-κB and IL-2 promoters and wild-type p65 gene, which have luciferase in the downstream region, was transfected into the nucleus of HEK293T cells, and then the cells were treated with the nt-p65-TMD recombinant fusion protein.

As a result, it could be seen that, when the cells were treated with the recombinant fusion protein, the expression of luciferase in the cells was effectively inhibited. This suggests that nt-p65-TMD acted as a competitive inhibitor of wild-type p65 to block the p65-binding site of each of the NF-κB and IL-2 promoters (see FIG. 6).

4-2: Confirmation of Inhibitory Effect Against Secretion of Inflammatory Cytokines in BV2 Microglial Cells BV2 microglial cells were treated with the nt-p65-TMD recombinant fusion protein of Example 1, and after 1 hour, the cells were treated and incubated with LPS (1 µg/ml, *E. coli* serotype O55:B5, Sigma-Aldrich) for 24 hours.

Figure 7:
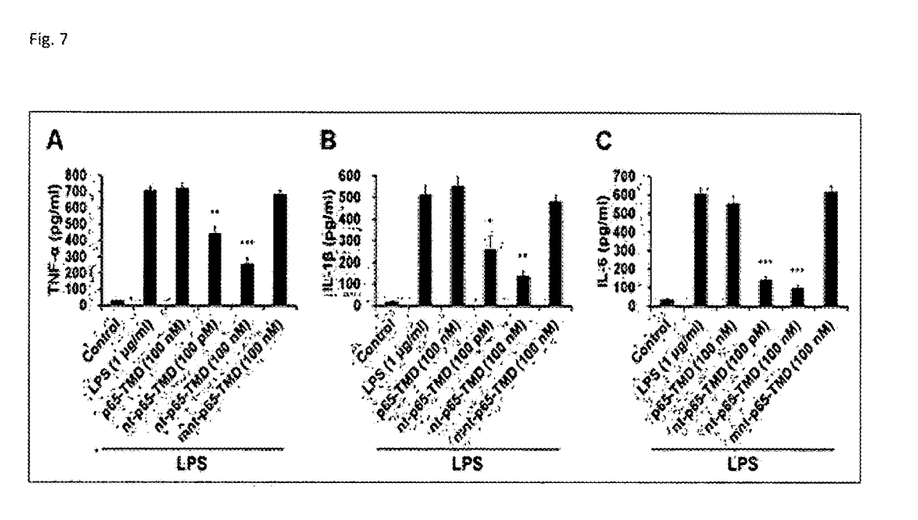
FIG. 7 shows the effect of the fusion protein (nt-p65-TMD) of the present invention on the inhibition of LPS-induced expression of TNF-α, IL-10 and IL-6.

As a result, it could be seen that the expression of TNF-α, IL-1β and IL-6, which are activated and expressed by LPS, was inhibited by the nt-p65-TMD recombinant fusion protein (see FIG. 7).

4-3: Confirmation of Specific Inhibitory Effect Against NF-κB Transcription Factor in Jurkat T Cells Whether or not the nt-p65-TMD recombinant fusion protein of Example 1 specifically inhibits the transcription of NF-κB activated by Jurkat T-cell activation stimulated by anti-CD3 (1 µg/ml, BD Pharmingen) and anti-CD28 (1 µg/ml, BD Pharmingen) was examined. When T cells are activated, not only NF-κB transcription but also NFAT transcription is activated. For this reason, if the nt-p65-TMD fusion protein inhibits only NF-κB transcription without influencing NFAT transcription, it can be seen that the nt-p65-TMD recombinant fusion protein acts as a specific competitive inhibitor of NF-κB. To confirm this fact, luciferase reporter gene was used. First, NF-κB and NFAT reporter genes having luciferase in the downstream region were transfected into the nucleus of Jurkat T cells by electroporation, and then the Jurkat T cells were stimulated with anti-CD3 and anti-CD28 and treated with the nt-p65-TMD recombinant fusion protein.

Figure 8A:
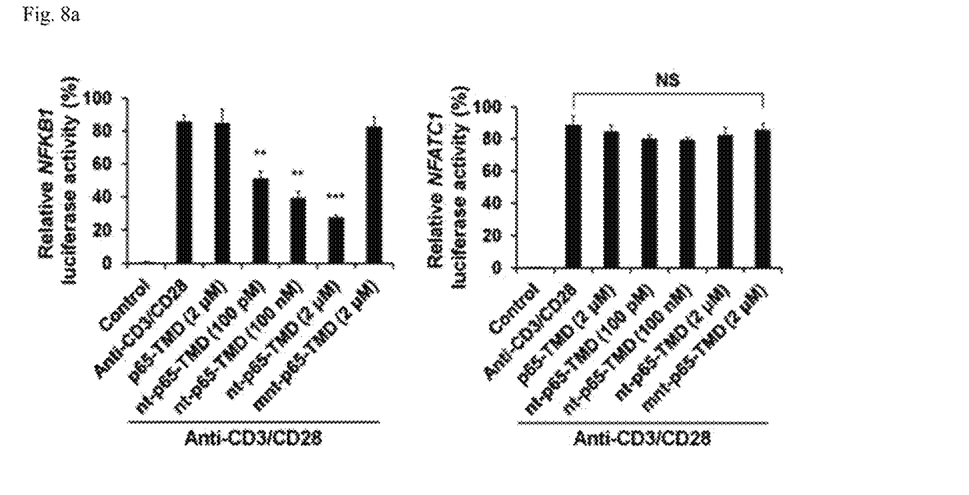
FIG. 8a shows results indicating that the fusion protein (nt-p65-TMD) of the present invention specifically inhibits NF-κB transcription induced by T-cell activation stimulated by anti-CD3/CD28.

As a result, it could be seen that, when the NF-κB-transfected cells were treated with the recombinant fusion protein, the expression of luciferase in the cells was effectively inhibited, but NFAT was not influenced by the recombinant fusion protein (see FIG. 8a).

4-4: Phosphorylation of Intracellular Signal Transduction Protein

In order to examine whether or not the nt-p65-TMD recombinant fusion protein of Example 1 is involved in tyrosine phosphorylation of proteins related to various intracellular signal transduction systems, Western blot analysis was performed. Jurkat T cells were treated with 2 µM of nt-p65-TMD for 1 hour, and then stimulated with anti-CD3 (2.5 µg/ml) and anti-CD28 (2.5 µg/ml), and whether or not tyrosine phosphorylation of ZAP-70, p38, JNK or ERK occurred was observed.

Figure 8B:
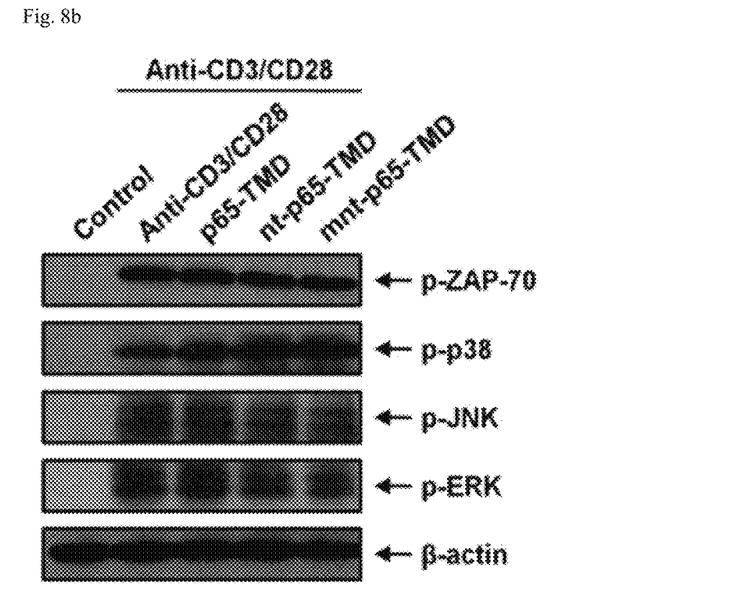
FIG. 8b show results indicating that fusion protein (nt-p65-TMD) of the present invention does not influence signal transduction pathways induced by T-cell activation stimulated by anti-CD3/CD28.

As a result, it could be seen that nt-p65-TMD did not influence phosphorylation of these proteins (see FIG. 8b).

4-5: Inhibition of Production of Cytokines (IL-2, IFN-γ, IL-4, IL-17A and IL-10) in Splenocytes Splenocytes isolated from the spleens of 6-8-week-old female C57BL/6 mice were treated with the nt-p65-TMD recombinant fusion protein of Example 1 for 1 hour to transduce the recombinant fusion protein into the cells. The cells were stimulated with anti-CD3 (1 µg/ml) and anti-CD28 (1 µg/ml), and then incubated for 72 hours. Next, the amounts of cytokines present in the medium were measured by ELISA.

Figure 9:
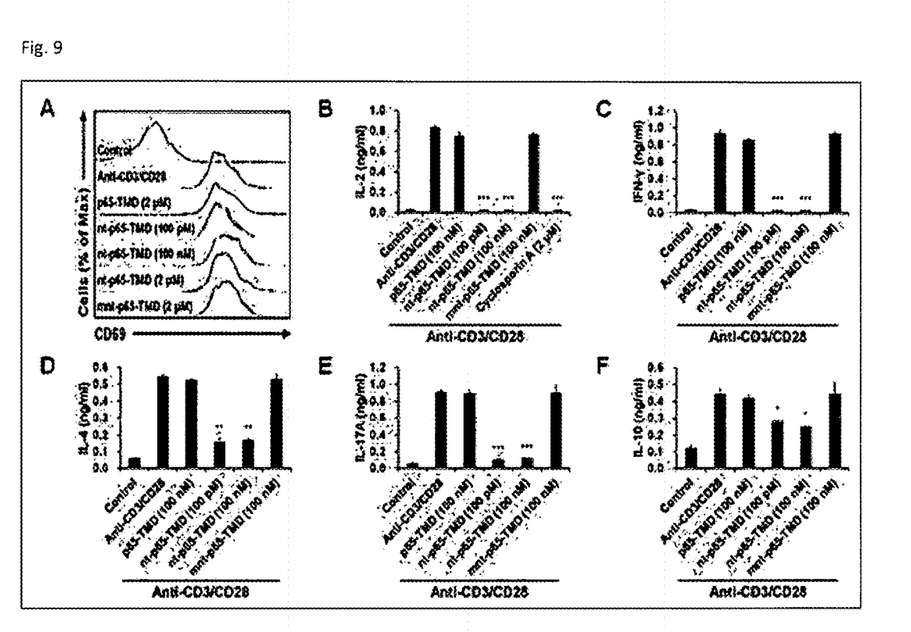
FIG. 9 shows results indicating that the fusion protein (nt-p65-TMD) of the present invention inhibits the expression of IL-2, IFN-γ, IL-4, IL-17A and IL-10, induced by T-cell activation stimulated by anti-CD3/CD28.

As a result, it could be seen that, when the cells were treated with nt-p65-TMD, the expression levels of IL-2, IFN-γ, IL-4, IL-17A and IL-10 in the cells were greatly inhibited. In addition, the expression level of CD69, which is indicative of T cell activation, was measured by FACS Calibur (BD Biosciences), and as a result, it could be seen that nt-p65-TMD did not influence the expression of CD69 in T cells (FIG. 9).

Example 5: Evaluation of Therapeutic Effect of nt-p65-TMD in Septic Shock Animal Models LPS (20 mg/kg) was injected intraperitoneally into 6-8-week-old male BALB/c mice to make septic shock animal models. After 2 hours and 14 hours, the nt-p65-TMD recombinant fusion protein of Example 1 was injected intraperitoneally into the animal models, followed by observation for 6 days.

As a result, it could be seen that, when the animal models were treated with nt-p65-TMD, the secretion of inflammatory cytokines (TNF-α, IL-1β and IL-6) was inhibited to thereby greatly increase the survival rate of the animal models (see FIG. 10).

Example 6: Acute Toxicity Test for Recombinant Fusion Protein

Using 6-week-old specific pathogen-free (SPF) rats obtained from the Daehan Experiment Supply Center, an acute toxicity test was performed in the following manner. The recombinant fusion protein of Example 1 was administered orally once to each animal group (consisting of two animals) at a dose of 1 g/kg, and then the death, clinical symptoms and weight changes of the animals were observed, and hematological tests and blood biochemical tests were performed. In addition, the animals were autopsied, and whether or not the abdominal organs and the thoracic organs were abnormal was visually observed.

As a result, in all the animals administered with the test substance, specific clinical symptoms or dead animals were not found, and in the weight change measurement, hematological tests, blood biochemical tests and autopsy findings, no change in toxicity was observed. Thus, it could be seen that the recombinant fusion protein of the present invention showed no toxicity in the rats even at a dose of 1 g/kg and that the minimum lethal dose ($LD_{50}$) upon oral administration thereof was 1 g/kg or more, suggesting that it is a safe substance.

The features and advantages of the present invention are as follows.

(a) The present invention provides a fusion protein comprising the transcription modulation domain of the NF-κB subunit p65 and a protein transduction domain, and the use thereof.

(b) The fusion protein of the present invention has the effects of inhibiting the transcription of NF-κB and IL-2 by competitive inhibition and inhibiting the LPS-induced secretion of inflammatory cytokines and also inhibiting the production of IL-2, IFN-γ, IL-4, IL-17A and IL-10 in splenocytes, and thus can be effectively used as a composition for the prevention or treatment of a disease related to NF-κB overactivity.

Although the present disclosure has been described in detail with reference to the specific features, it will be apparent to those skilled in the art that this description is only of a preferred embodiment thereof, and does not limit the scope of the present invention. Thus, the substantial scope of the present invention will be defined by the appended claims and equivalents thereof.

REFERENCES

Park et al., Intranuclear interactomic inhibition of NF-κB suppresses LPS-induced severe sepsis, *Biochemical and Biophysical Research Communications*, 2015; 464:711-717.

---

What is claimed is:

1. A fusion protein comprising a transcription modulation domain of NF-κB and a protein transduction domain, wherein the fusion protein inhibits NF-κB transcription by competitive inhibition, wherein the fusion protein has the amino acid sequence comprising SEQ ID NO:5.

2. A pharmaceutical composition for treatment of a disease related to NF-κB overactivity, the composition comprising the fusion protein of claim 1 as an active ingredient, wherein the disease related to NF-κB overactivity is septic shock or inflammatory disease,
wherein the inflammatory disease is selected from the group consisting of allergic asthma, allergic nasitis, atopic dermatitis, systemic lupus erythematosus, rheumatoid arthritis, ulcerative colitis, dacryoadenitis, Alzheimer's disease, stroke, arteriosclerosis, vascular restenosis, type I diabetes, type II diabetes, urticaria, conjunctivitis, psoriasis, systemic inflammatory response syndrome, polymyositis, dermatomyositis, polyarthritis nodosa, mixed connective tissue disease, Sjogren's syndrome, gout, Parkinson's disease, amyotrophic lateral sclerosis, diabetic retinopathy, multiple sclerosis, Crohn's disease, chronic thyroiditis, Celiac disease, radiation-induced disorders, hemangioma, reperfusion injury, and cardiac hypertrophy.

* * * * *

SEQUENCE LISTING

<160> NUMBER OF SEQ ID NOS: 6

<210> SEQ ID NO 1
<211> LENGTH: 187
<212> TYPE: PRT
<213> ORGANISM: Artificial Sequence
<220> FEATURE:
<223> OTHER INFORMATION: Amino acid sequence of p65 transcription modulation domain

<400> SEQUENCE: 1

Met Asp Asp Leu Phe Pro Leu Ile Phe Pro Ser Glu Pro Ala Gln Ala
1               5                   10                  15

Ser Gly Pro Tyr Val Glu Ile Ile Glu Gln Pro Lys Gln Arg Gly Met
                20                  25                  30

Arg Phe Arg Tyr Lys Cys Glu Gly Arg Ser Ala Gly Ser Ile Pro Gly
            35                  40                  45

Glu Arg Ser Thr Asp Thr Thr Lys Thr His Pro Thr Ile Lys Ile Asn
        50                  55                  60

Gly Tyr Thr Gly Pro Gly Thr Val Arg Ile Ser Leu Val Thr Lys Asp
65                  70                  75                  80

Pro Pro His Arg Pro His Pro His Glu Leu Val Gly Lys Asp Cys Arg
                85                  90                  95

```
Asp Gly Tyr Tyr Glu Ala Asp Leu Cys Pro Asp Arg Ser Ile His Ser
            100                 105                 110

Phe Gln Asn Leu Gly Ile Gln Cys Val Lys Lys Arg Asp Leu Glu Gln
        115                 120                 125

Ala Ile Ser Gln Arg Ile Gln Thr Asn Asn Pro Phe His Val Pro
    130                 135                 140

Ile Glu Glu Gln Arg Gly Asp Tyr Asp Leu Asn Ala Val Arg Leu Cys
145                 150                 155                 160

Phe Gln Val Thr Val Arg Asp Pro Ala Gly Arg Pro Leu Leu Leu Thr
                165                 170                 175

Pro Val Leu Ser His Pro Ile Phe Asp Asn Arg
            180                 185
```

<210> SEQ ID NO 2
<211> LENGTH: 561
<212> TYPE: DNA
<213> ORGANISM: Artificial Sequence
<220> FEATURE:
<223> OTHER INFORMATION: Nucleotide sequence of p65 transcription
      modulation domain

<400> SEQUENCE: 2

```
atggacgatc tgtttcccct catctttccc tcagagccag cccaggcttc tgggccttat      60
gtggagatca tcgaacagcc gaagcaacgg ggcatgcgat ccgctataa atgcgagggg     120
cgctcagcgg gcagtattcc tggcgagaga agcacagata ccaccaagac acccccacc     180
atcaagatca atggctacac aggaccagga acagttcgaa tctccctggt caccaaggat     240
ccacctcacc ggcctcatcc acatgaactt gtggggaagg actgccggga tggctactat     300
gaggctgacc tctgcccaga ccgcagtatc catagcttcc agaacctggg gatccagtgt     360
gtgaagaagc gagacctgga gcaagccatt agccagcgaa tccagaccaa caataacccc     420
tttcacgttc ctatagagga gcagcgcggg gactatgact tgaatgcagt gcgcctctgc     480
ttccaggtga cagtgcggga cccagcaggc aggcccctcc tcctgacccc tgtcctctca     540
catccgattt ttgataaccg g                                              561
```

<210> SEQ ID NO 3
<211> LENGTH: 11
<212> TYPE: PRT
<213> ORGANISM: Artificial Sequence
<220> FEATURE:
<223> OTHER INFORMATION: Amino acid sequence of Hph-1

<400> SEQUENCE: 3

```
Tyr Ala Arg Val Arg Arg Arg Gly Pro Arg Arg
1               5                   10
```

<210> SEQ ID NO 4
<211> LENGTH: 33
<212> TYPE: DNA
<213> ORGANISM: Artificial Sequence
<220> FEATURE:
<223> OTHER INFORMATION: Nucleotide sequence of Hph-1

<400> SEQUENCE: 4

```
tatgcacgtg ttcggaggcg tggaccccgc cgc                                   33
```

<210> SEQ ID NO 5
<211> LENGTH: 235
<212> TYPE: PRT
<213> ORGANISM: Artificial Sequence
<220> FEATURE:
<223> OTHER INFORMATION: Amino acid sequence of nt-p65-TMD

<400> SEQUENCE: 5

```
Met Gly Ser Ser His His His His His His Ser Ser Gly Leu Val Pro
1               5                   10                  15

Arg Gly Ser His Met Ala Ser Gly Tyr Ala Arg Val Arg Arg Arg Gly
            20                  25                  30

Pro Arg Arg Gly Gly Ser Asp Tyr Lys Asp Asp Asp Lys Glu Phe
        35                  40                  45

Met Asp Asp Leu Phe Pro Leu Ile Phe Pro Ser Glu Pro Ala Gln Ala
    50                  55                  60

Ser Gly Pro Tyr Val Glu Ile Ile Glu Gln Pro Lys Gln Arg Gly Met
65                  70                  75                  80

Arg Phe Arg Tyr Lys Cys Glu Gly Arg Ser Ala Gly Ser Ile Pro Gly
                85                  90                  95

Glu Arg Ser Thr Asp Thr Thr Lys Thr His Pro Thr Ile Lys Ile Asn
            100                 105                 110

Gly Tyr Thr Gly Pro Gly Thr Val Arg Ile Ser Leu Val Thr Lys Asp
        115                 120                 125

Pro Pro His Arg Pro His Pro His Glu Leu Val Gly Lys Asp Cys Arg
    130                 135                 140

Asp Gly Tyr Tyr Glu Ala Asp Leu Cys Pro Asp Arg Ser Ile His Ser
145                 150                 155                 160

Phe Gln Asn Leu Gly Ile Gln Cys Val Lys Lys Arg Asp Leu Glu Gln
                165                 170                 175

Ala Ile Ser Gln Arg Ile Gln Thr Asn Asn Asn Pro Phe His Val Pro
            180                 185                 190

Ile Glu Glu Gln Arg Gly Asp Tyr Asp Leu Asn Ala Val Arg Leu Cys
        195                 200                 205

Phe Gln Val Thr Val Arg Asp Pro Ala Gly Arg Pro Leu Leu Leu Thr
    210                 215                 220

Pro Val Leu Ser His Pro Ile Phe Asp Asn Arg
225                 230                 235
```

<210> SEQ ID NO 6
<211> LENGTH: 708
<212> TYPE: DNA
<213> ORGANISM: Artificial Sequence
<220> FEATURE:
<223> OTHER INFORMATION: Nucleotide sequence of nt-p65-TMD

<400> SEQUENCE: 6

```
atgggcagca gccatcatca tcatcatcac agcagcggcc tggtgccgcg cggcagccat    60
atggctagcg gctatgcacg tgttcggagg cgtggacccc gccgcggcgg atccgactac   120
aaggacgacg atgacaagga attcatggac gatctgtttc ccctcatctt tccctcagag   180
ccagcccagg cttctgggcc ttatgtggag atcatcgaac agccgaagca acggggcatg   240
cgattccgct ataaatgcga ggggcgctca gcgggcagta ttcctggcga gagaagcaca   300
gataccacca agacacaccc caccatcaag atcaatggct acacaggacc aggaacagtt   360
cgaatctccc tggtcaccaa ggatccacct caccggcctc atccacatga acttgtgggg   420
aaggactgcc gggatggcta ctatgaggct gacctctgcc cagaccgcag tatccatagc   480
ttccagaacc tggggatcca gtgtgtgaag aagcgagacc tggagcaagc cattagccag   540
cgaatccaga ccaacaataa ccccttcac gttcctatag aggagcagcg cggggactat   600
```

```
gacttgaatg cagtgcgcct ctgcttccag gtgacagtgc gggacccagc aggcaggccc    660
ctcctcctga ccctgtcct ctcacatccg atttttgata accggtag                 708
```